(12) United States Patent
Thieme et al.

(10) Patent No.: US 8,766,655 B2
(45) Date of Patent: Jul. 1, 2014

(54) CONDUCTIVE CONDUCTIVITY SENSOR

(75) Inventors: André Thieme, Borna (DE); Marco Völker, Schwetzingen (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 13/550,990

(22) Filed: Jul. 17, 2012

(65) Prior Publication Data

US 2013/0021047 A1  Jan. 24, 2013

(30) Foreign Application Priority Data

Jul. 18, 2011  (DE) .................. 10 2011 079 346

(51) Int. Cl.
*G01R 27/08*   (2006.01)
(52) U.S. Cl.
USPC ........................................................... 324/724
(58) Field of Classification Search
USPC ................. 324/724, 600, 452–453, 500, 514, 324/754.04
See application file for complete search history.

(56) References Cited

U.S. PATENT DOCUMENTS

| | | | |
|---|---|---|---|
| 3,939,408 A | 2/1976 | Brown | |
| 5,572,491 A * | 11/1996 | Karibe et al. | 369/13.28 |
| 7,355,415 B2 * | 4/2008 | Boyle et al. | 324/707 |
| 7,965,167 B2 * | 6/2011 | Volker et al. | 336/229 |
| 8,382,683 B2 * | 2/2013 | Freeman et al. | 600/583 |
| 8,629,572 B1 * | 1/2014 | Phillips | 290/53 |
| 2011/0309848 A1 * | 12/2011 | Eberheim et al. | 324/724 |
| 2013/0176836 A1 * | 7/2013 | Zheludev et al. | 369/13.17 |

FOREIGN PATENT DOCUMENTS

| | | |
|---|---|---|
| DE | 10309769 A1 | 11/2003 |
| DE | 102008054659 A1 | 6/2010 |
| GB | 1387825 | 3/1975 |

OTHER PUBLICATIONS

German Search Report.

* cited by examiner

*Primary Examiner* — Melissa Koval
*Assistant Examiner* — Trung Nguyen
(74) *Attorney, Agent, or Firm* — Bacon & Thomas, PLLC

(57) ABSTRACT

A conductive conductivity sensor, comprising: a probe immersible in a measured medium. The probe has an inner space, which is connected to an environment of the probe via at least one opening leading out from the inner space and in which are arranged two electrodes, which are supplied with an alternating voltage during measurement operation and which have inner surfaces facing into the inner space and outwardly facing outer surfaces covered by insulation, wherein the inner surfaces have edge surfaces adjoining the openings. Measuring characteristics of the conductivity sensor have a smallest possible dependence on objects arranged in the vicinity of the conductivity sensor. At least the edge surfaces adjoining one of the openings have a surface geometry directing thereon beginning or ending, electric field lines in a direction facing away from such opening and into the inner space.

10 Claims, 9 Drawing Sheets

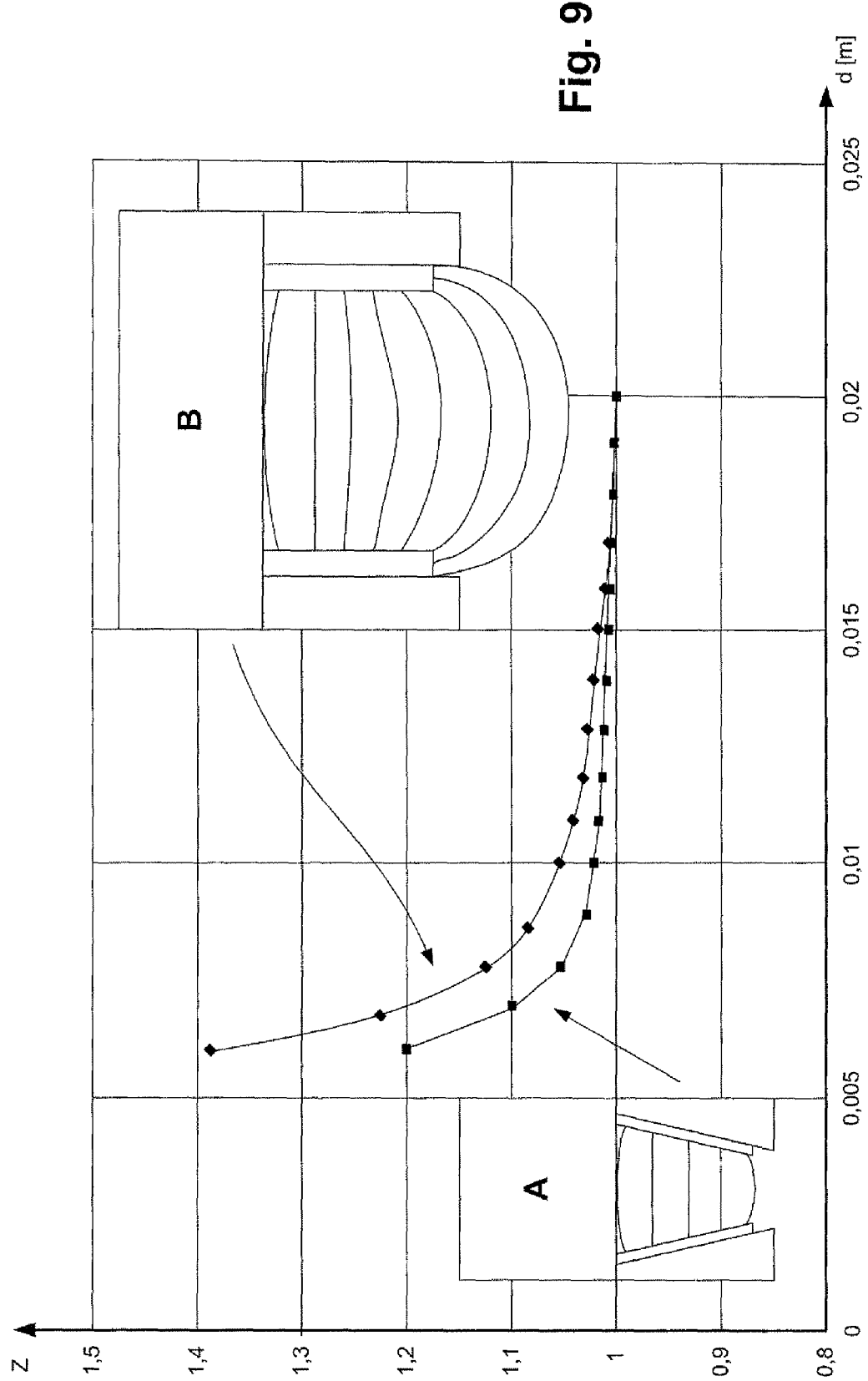

CONDUCTIVE CONDUCTIVITY SENSOR

TECHNICAL FIELD

The invention relates to a conductive conductivity sensor having a probe that is immersible in a measured medium, wherein the probe has an inner space, which is connected with an environment of the probe via at least one opening leading outwards from the inner space. Two electrodes, which are supplied with an alternating voltage during measurement operation, are arranged in the inner space. The electrodes have inner surfaces facing into the inner space and outer surfaces, which face outwards and are covered by insulation. The inner surfaces have edge surfaces adjoining the openings.

BACKGROUND DISCUSSION

Conductive conductivity sensors are utilized in various applications for measuring conductivity of a medium.

The best known conductive conductivity sensors are the so called two electrode or four electrode sensors.

Two electrode sensors have two electrodes immersed in the medium and supplied with an alternating voltage during measurement operation. A measuring electronics connected to the two electrodes measures an electrical impedance of the conductivity measurement cell, from which a specific resistance or a specific conductance of the medium located in the measuring cell is then ascertained based on a cell constant determined earlier by the geometry and the character of the given measuring cell.

Four electrode sensors have four electrodes immersed in the medium during measurement operation, of which two electrodes are operated as so called electrical current electrodes and two electrodes are operated as so called voltage electrodes. During measurement operation, an alternating voltage is placed between the two electrical current electrodes, and therewith an alternating electrical current is fed into the medium. The electrical current fed in effects a potential difference lying between the voltage electrodes. The potential difference is preferably ascertained using a currentless measurement. Also here, by means of a measuring electronics connected to the electrical current electrodes and voltage electrodes, the impedance of the conductivity measurement cell is ascertained from the alternating electrical current fed in and the measured potential difference. Then, from the impedance, a specific resistance or a specific conductance of the medium located in the measuring cell is ascertained based on a cell constant determined earlier and resulting from the geometry and the character of the measuring cell.

During measurement operation, electric fields, whose field lines regularly extend out from the inner space of the measuring cell, form between the electrodes.

If such a conductivity sensor is operated in the vicinity of another object, such as e.g. a container wall, there is an influencing of the electric field lines by the object, and therewith an influencing of the measurement. This influencing, which is essentially dependent on the geometric arrangement of the object, its separation from the sensor, and its electrical conductivity, is regularly determined today using a complicated calibration method at the location of use, and therefrom, for example, an installation factor is determined, with which the influencing can be compensated in the following measurements.

Moreover, DE 10 2008 054 659 A1 describes reducing the influence of objects located in the environment of a conductive conductivity sensor by arranging planar electrodes parallel to one another on mutually opposing inner surfaces of an externally accessible cavity in an electrically insulating probe body.

This offers the advantage that the field lines extend essentially within the cavity between the electrodes, compared to conductivity sensors having electrodes lying at least partially completely free or protruding out from a probe body, such that they include a distinct free field outside of the probe body.

Also here, the spatial region occupied by the field lines is, however, clearly greater than the inner space of the cavity enclosed by the oppositely lying, flat electrodes.

In order to prevent an influencing by objects in the vicinity of the conductivity sensor, it is necessary to arrange the electrodes with a sufficient separation from the outwardly facing openings of the inner space. Among other things, this results in a certain minimum structural size of the conductivity sensors. It is not possible, without more, to consider using sizes below this minimum.

SUMMARY OF THE INVENTION

It is an object of the invention to provide a conductive conductivity sensor, whose measuring characteristics have a smallest possible dependence on objects arranged in the vicinity of the conductivity sensor.

For this, the invention resides in a conductive conductivity sensor, comprising
- a probe immersible in a measured medium,
- which has an inner space,
- which is connected with an environment of the probe via at least one opening leading outwards from the inner space, and
- in which are arranged two electrodes, which are supplied with an alternating voltage during measurement operation and which have inner surfaces facing into the inner space and outwardly facing outer surfaces covered by insulation,
- wherein the inner surfaces have edge surfaces adjoining the openings, and
wherein, according to the invention, at least the edge surfaces adjoining one of the openings have a surface geometry directing thereon beginning or ending, electric field lines in a direction facing away from such opening and into the inner space.

In a preferred embodiment, all edge surfaces of the inner surfaces of the electrodes neighboring the openings have a surface geometry directing electric field lines, which begin or end thereon, in a direction facing away from the respective opening and into the inner space.

In an additional embodiment, surface normals of the edge surfaces having the surface geometry of the invention point in a direction away from the respective opening and into the inner space.

In a further development of the invention the inner surfaces of the electrodes have a surface geometry, which focuses electric field lines into the inner space.

In a first variant of the invention, the inner surfaces of the electrodes are concave.

In a second variant of the invention, the electrodes have a planar base, on which adjoins, on at least one side neighboring one of the openings, an edge surface inclined in a direction facing away from the opening and into the inner space.

In a preferred further development of the invention, the electrodes are arranged mutually opposed and inclined relative to one another, wherein each of the two electrodes has totally one orientation facing in a direction away from one and the same opening and into the inner space.

In a further development of the last further development, each of the electrodes is inclined in the direction of an electrically insulating probe wall, which closes off the inner space from the outside on one side.

In an embodiment of the preferred further development
the electrodes are electrical current electrodes, via which an alternating electrical current can be fed into a medium located in the inner space through application of an alternating voltage to the electrodes during measurement operation; and,
in the inner space, two voltage electrodes are provided, via which a potential difference lying thereacross due to the alternating current applied to the medium can be tapped during measurement operation.

BRIEF DESCRIPTION OF THE DRAWINGS

In a further development of the last embodiment, the voltage electrodes are arranged on the probe wall.

The invention and its advantages will be now explained in greater detail based on the figures of the drawing, which present six examples of embodiments; equal elements are provided with the equal reference characters in the figures. The figures of the drawing show as follows:

FIG. 9 is a comparison of normalized cell constants of two conductivity probes as a function of separation from an object located thereunder.

DETAILED DISCUSSION IN CONJUNCTION WITH THE DRAWINGS

The invention will now be described based on a number of examples of embodiments of conductive, two electrode conductivity sensors as well as conductive, four electrode conductivity sensors. The invention is also analogously applicable to conductivity sensors having other numbers of electrodes.

Figure 1:
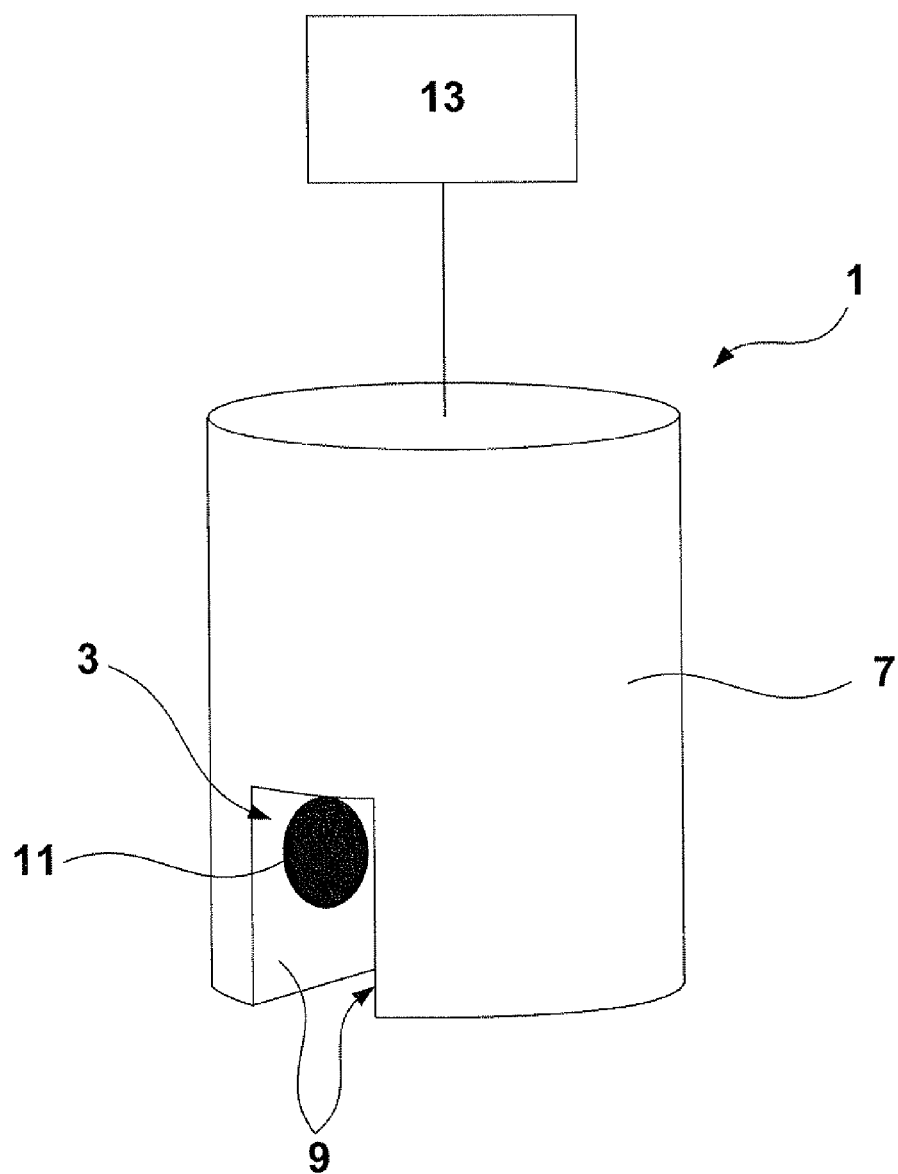
FIG. 1 is a schematic drawing of a conductive conductivity sensor of the invention.
Figure 1:
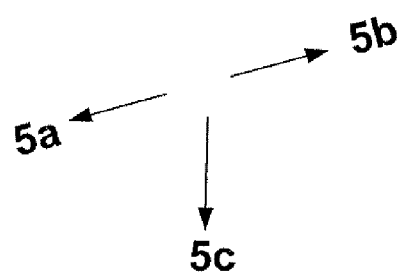

FIG. 1 shows a view of a conductive two electrode conductivity sensor of the invention. The conductivity sensor has a probe 1 immersible in a measured medium. Probe 1 has an inner space 3, which is opened to the environment of probe 1 via at least one opening 5 leading out from inner space 3.

Upon immersion of probe 1 into the medium, the medium penetrates into inner space 3 via openings 5, and fills inner space 3.

In the example of an embodiment shown here, probe 1 has a cylindrical probe body 7 comprising an electrical insulator, which has an open rectangular cavity on an end leading diagonally through probe body 7 to the end of probe 1. Inner space 3 is located between two mutually opposing, planparallel, inner walls 9 of the cavity and, in the illustrated example of an embodiment, is opened to the environment by an opening 5a facing the front in the drawing (out from the plane of the drawing), an opening 5b lying opposite this facing the back in the drawing (into in the plane of the drawing) and, consequently, not visible in the figure and an opening 5c, which connects both openings 5a, 5b with one another, facing down in the drawing on the lower end of the probe 1. The three openings 5a, 5b, 5c are represented here by arrows facing in their directions opening out from inner space 3.

Provided in inner space 3 are two electrodes 11, whose inner surfaces face into inner space 3, and whose outwardly facing, outer surfaces are covered by probe body 7, which is an insulator in the illustrated example of an embodiment. Measuring electronics 13—here only schematically shown— is connected to electrodes 11. During measurement operation, measuring electronics 13 supplies electrodes 11 with an alternating voltage, determines an electrical impedance of the conductivity measurement cell formed by the immersion of probe 1 in the medium, and ascertains a specific resistance or a specific conductance of the medium located in the measuring cell based on a cell constant Z determined earlier and resulting from the geometry and the character of the given measuring cell.

The inner surfaces of electrodes 11 have, in each case, edge surfaces adjoining the individual openings 5a, 5b, 5c. According to the invention, the edge surfaces neighboring at least one of openings 5a, 5b or 5c have a surface geometry directing electric field lines, which begin or end thereon, in a direction away from the outwardly facing opening 5a, 5b, or 5c into the interior of inner space 3.

This preferably happens with a surface geometry, in the case of which the surface normals to these edge surfaces point into the inner space 3 in a direction away from the respectively neighboring opening 5a, 5b, 5c.

Since electrodes 11 are equipotential surfaces, on which electric field lines always end perpendicularly, the electric field lines in the immediate vicinity of electrodes 11 are constrained to extend parallel to the surface normals to electrodes 11. Correspondingly, the field lines at each opening 5a, 5b, 5c, on which the edge surfaces of the inner surfaces of electrodes 11 neighboring thereto face in a direction facing away from this opening 5a, 5b, 5c into interior 3, face into inner space 3. This effects a clear reduction of field lines emerging from the respective opening 5a, 5b, 5c.

A greatest possible reduction of the total of field lines emerging from inner space 3 is, thus, achieved by having not only the edge surfaces neighboring one of the openings 5a, 5b or 5c, but, rather, all edge surfaces neighboring the openings 5a, 5b, 5c have surface geometries embodied in the manner of the invention. In this case, the surface normals on all edge surfaces respectively neighboring the openings 5a, 5b, 5c point away from their adjoining opening 5a, 5b, 5c and into inner space 3.

The invention effects a targeted orientation and preferably also a focusing of the field lines forming during measurement operation between electrodes 11 into inner space 3 of probe 1 via the surface geometry of the edge surfaces.

The surface geometry of the invention for the edge surfaces of electrodes 11 can be implemented by varied formations of electrodes 11 and adapted to varied embodiments of openings 5 of inner space 3.

For this, for example, electrodes having a planar base can be applied, which is surrounded, on at least one side, preferably all sides, adjoining an opening 5, by an edge surface inclined into inner space 3 relative to the base in a direction facing away from, in each case, the adjoining opening 5.

Figure 2:
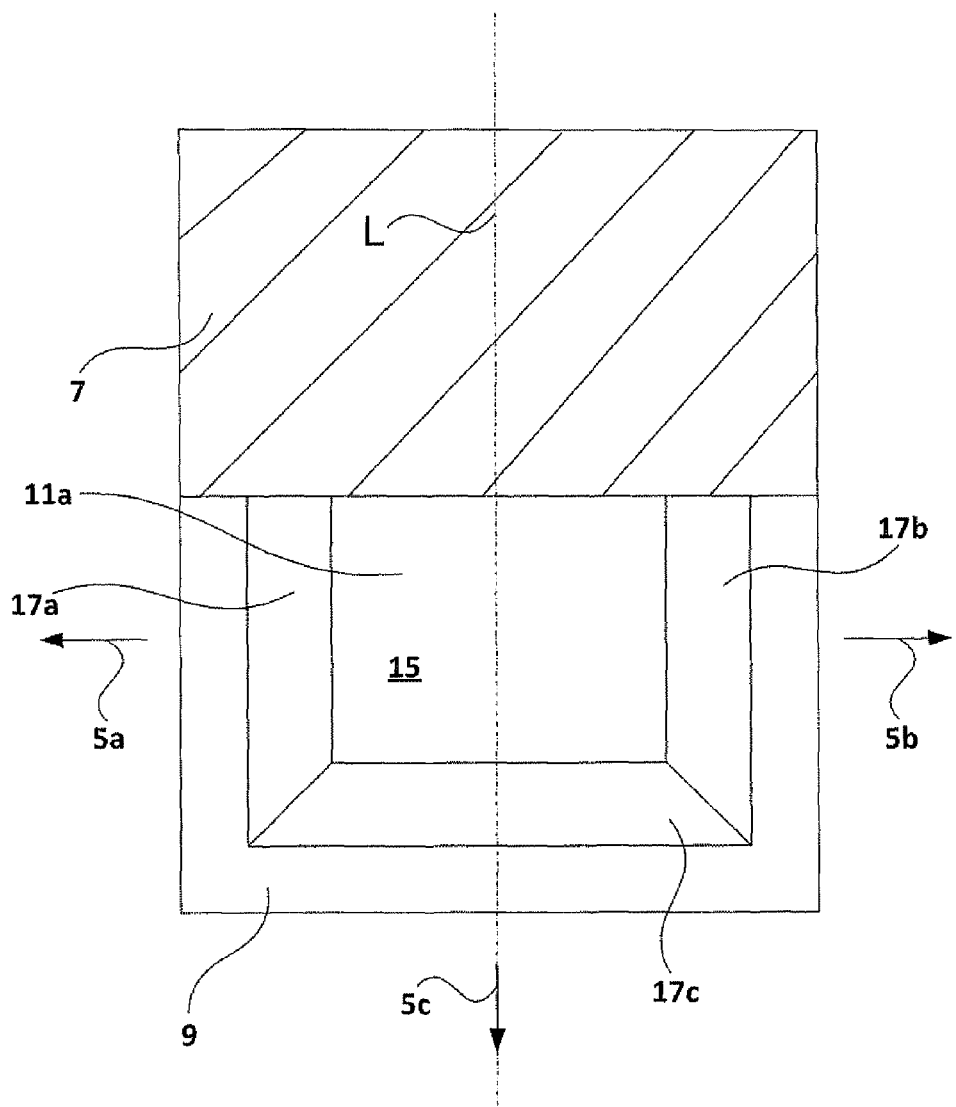
FIG. 2 is a longitudinal section through a probe according to FIG. 1 having an electrode with planar base and thereto adjoining edge surfaces inclined into the inner space.
Figure 3:
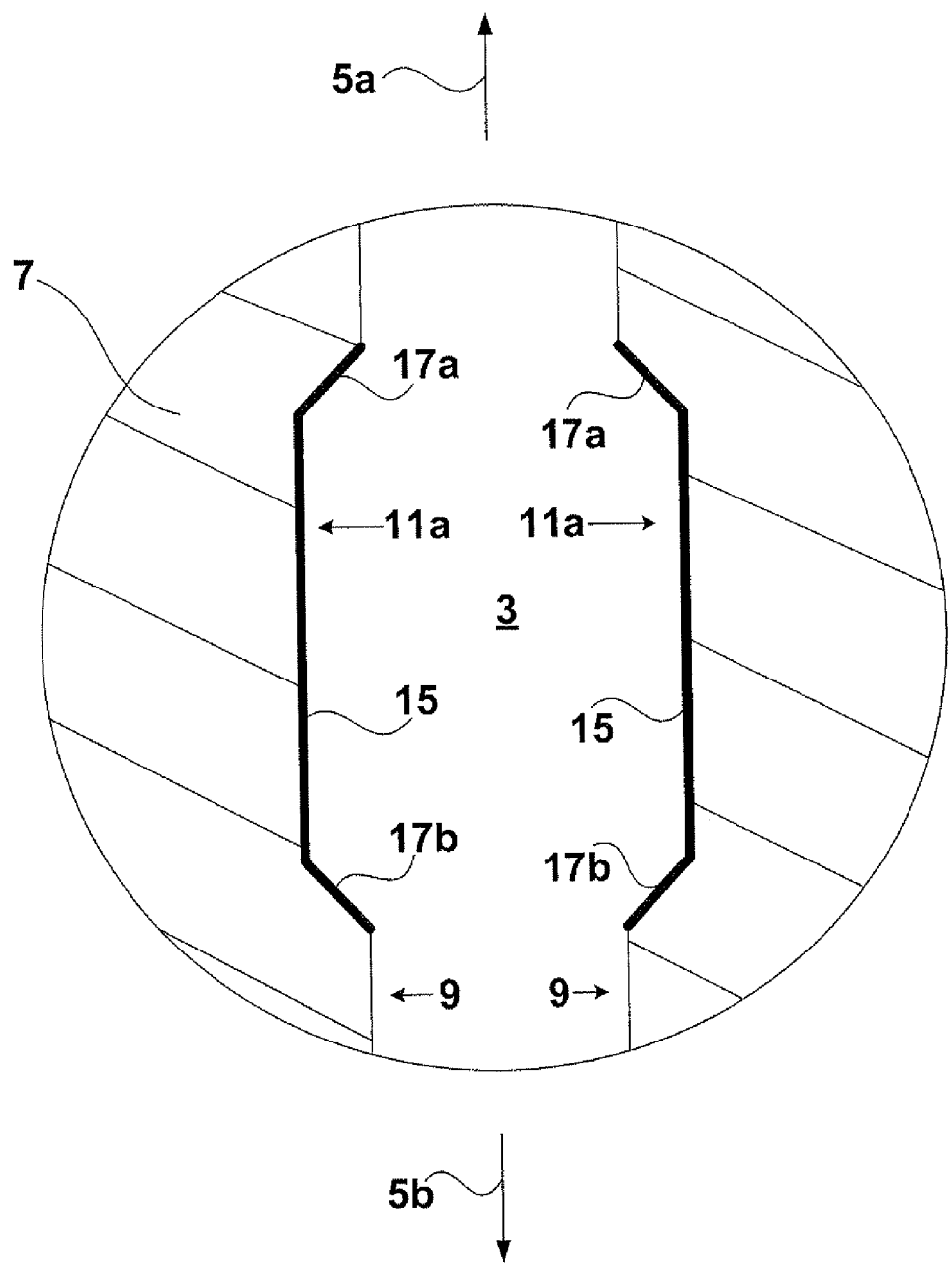
FIG. 3 is a sectional drawing of the probe of FIG. 1 having the electrode of FIG. 2 taken in a plane perpendicular to the probe longitudinal axis at the height of the center of the mutually opposing electrodes.

A rectangular example of an embodiment for this, adapted to the three sides of open inner space 3 of the example of an embodiment illustrated in FIG. 1 is presented in FIGS. 2 and 3. FIG. 2 shows a longitudinal section through probe 1 in the plane of inner wall 9. The electrode 11a shown, which is arranged centrally on inner wall 9, has a planar rectangular base 15, which is surrounded on its three sides adjoining openings 5a, 5b, 5c, here symbolized by arrows, of inner space 3, in each case, by an edge surface 17a, 17b, 17c inclined into inner space 3 in a direction, in each case, facing away from the adjoining opening 5a, 5b, or 5c. FIG. 3 shows for this a sectional drawing of probe 1 of FIG. 1 taken in a plane extending perpendicularly to the probe longitudinal axis L at the height of the centers of the mutually opposing, equally shaped electrodes 11a.

Figure 4:
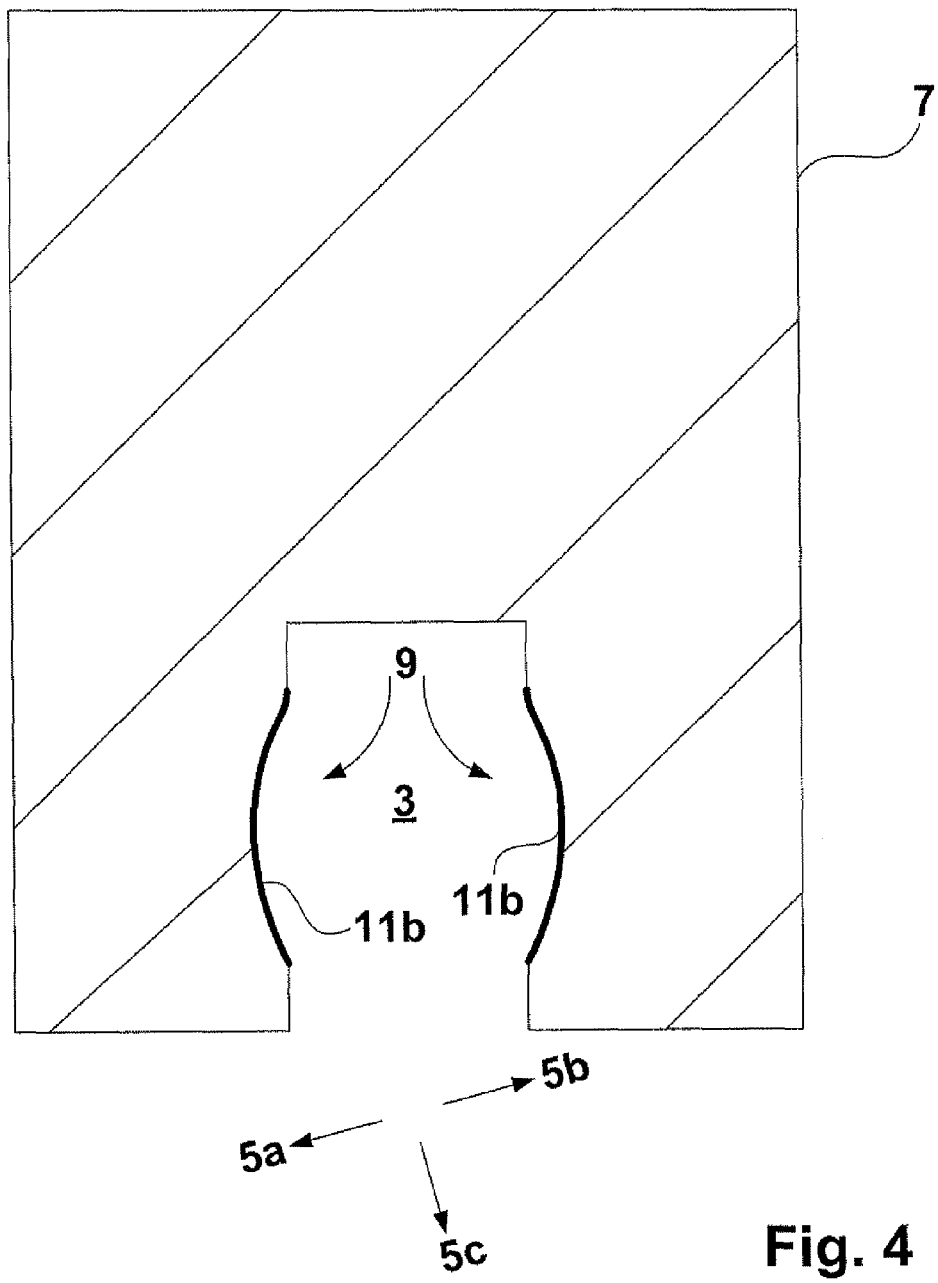
FIG. 4 is a conductivity probe having concave, mutually opposing electrodes.

FIG. 4 shows a longitudinal section through another form of embodiment adapted to the rectangular, three sides open, inner space 3 of FIG. 1. In this case, again, two equally formed, mutually facing, electrodes 11b arranged centrally on inner walls 9 of inner space 3 are provided. In contrast to the preceding example of an embodiment, electrodes 11b, however, do not have planar base surfaces, but, instead, have totally concave inner surfaces.

In this form, the surface normals on all outer edge surfaces of electrodes 11b point in a direction away from the adjoining opening 5, in each case, into inner space 3. Through this concave shape the field lines are directed in the edge regions neighboring openings 5a, 5b, 5c into inner space 3 and supplementally focused on all sides into inner space 3. Moreover, concave electrode inner surfaces offer the advantage of a high symmetry, which is advantageous as regards the calibration of the measuring cell and the accuracy of measurement achievable therewith.

Alternatively or in combination with the variants already described, a surface geometry of the invention for the edge surfaces of the inner surfaces of the electrodes neighboring one of openings 5 can also be effected such that electrodes 11 are arranged mutually opposed and totally inclined relative to one another. In such case, electrodes 11, as a whole, are oriented, in each case, in such a manner that they face in a direction away from such opening 5 into inner space 3.

Preferably, an electrode orientation is selected, in which the surface normals on the inner surfaces of electrodes 11 point in the direction of an electrically insulating probe wall, which closes off the inner space 3 from the outside on one side. This variant offers the advantage that the field lines are not only oriented in a direction facing away from this opening 5, but are also oriented in the direction of the probe wall at the same time. There, independently of the location of use of probe 1, always the same conditions for the field expansion, reign, due to the insulation by the probe wall.

For example, the upward interior border formed by the solid part of probe body 7 adjoining inner space 3 is suited as such probe wall.

Figure 5:
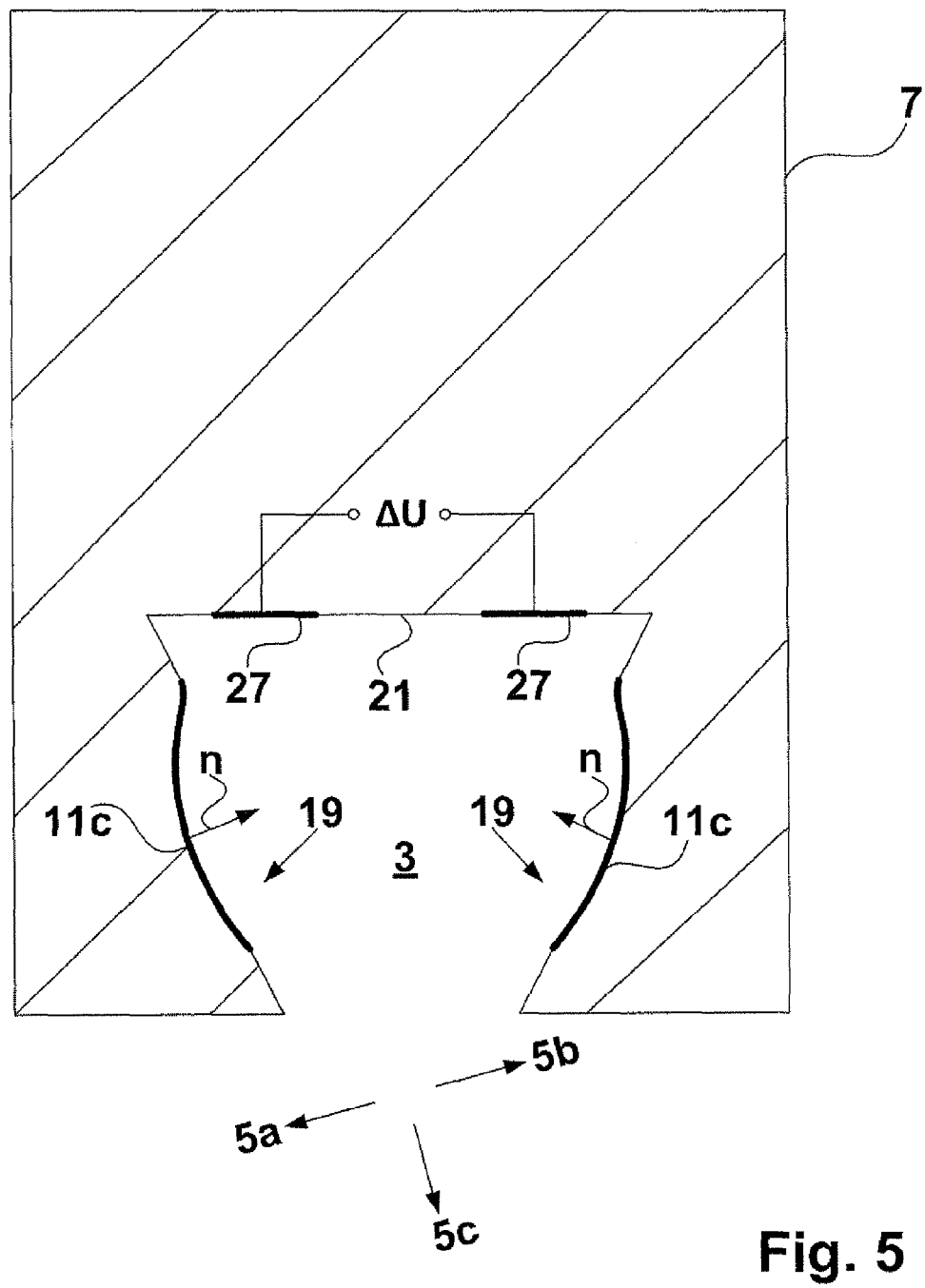
FIG. 5 is a conductivity probe having concave mutually opposing electrodes inclined relative to one another in the direction of an upper probe wall.

FIG. 5 shows a longitudinal section through an example of an embodiment in this connection. Exactly as in the example of an embodiment illustrated in FIG. 1, probe 1 here also has, for example, a cylindrical probe body 7 comprising an electrical insulator, which terminally has an open cavity diagonally leading through probe body 7 at the lower end of probe 1. Inner space 3 is also located here between mutually opposing inner walls 19 of the cavity and in the illustrated example of an embodiment is opened to the environment by an opening 5a facing forward in the drawing, an opening 5b lying oppositely this facing backwards in the drawing and an opening 5c connecting the two openings 5a, 5b with one another directed down in the drawing at the lower end of probe 1. Inner space 3 is closed off above by insulating probe wall 21 formed by the solid part of probe body 7 adjoining inner space 3. In contrast to the examples of embodiments illustrated in FIGS. 1 to 4, inner walls 19 here, however, are not planparallel but, instead, are arranged inclined relative to one another, wherein the separation between oppositely lying inner walls 19 increases in the direction of probe wall 21. The orientation of electrodes 11c corresponding to the inclination of inner walls 19 facing in the direction facing away from opening 5c into inner space 3 in the direction of probe wall 21 is here illustrated by the surface normals n drawn in at the electrode centers. Both electrodes 11c have concave inner surfaces and are centrally arranged on inner walls 19 of inner space 3.

Figure 6:
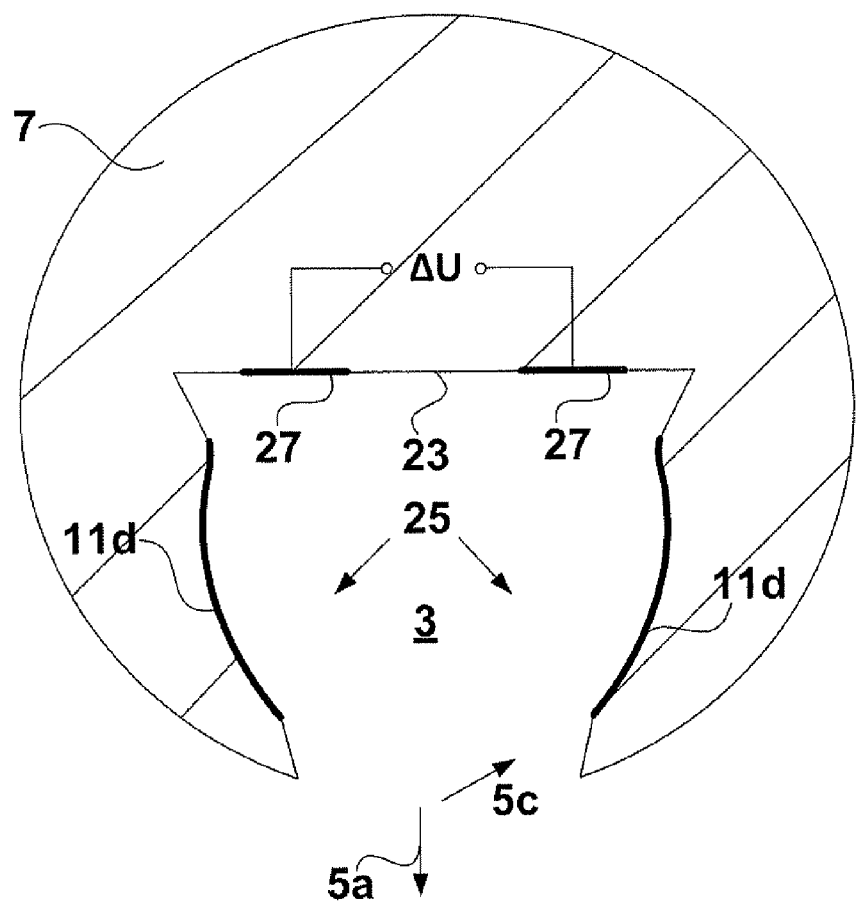
FIG. 6 is a conductivity probe having concave mutually opposing electrodes inclined relative to one another in the direction of a rear probe wall.

In probes, which, in contrast with the variant illustrated in FIG. 1, are equipped with an additional rear probe wall 23 closing off opening 5b in FIG. 1, the orientation of the field lines can also naturally be in the direction of this probe wall 23. FIG. 6 shows, for this, a cross section through an example of an embodiment of such a probe in a plane extending perpendicularly to the probe longitudinal axis L at the height of the center of electrodes 11d, which are likewise concave here.

Exactly as in the example of an embodiment illustrated in FIG. 1, the probe here has, for example, also a cylindrical probe body 7 comprising an electrical insulator, which terminally has an open cavity diagonally leading through probe body 7 at the lower end of probe 1. Inner space 3 is here also located between inner walls 25 of the cavity, which lie opposite one another and are inclined relative to one another, and is opened to the environment on the lower end of probe 1 only by a frontal opening 5a and a downwards directed opening 5c. Inner space 3 is closed off above by the solid part of probe body 7 adjoining inner space 3 and behind by insulating probe wall 23. Opening 5b in the earlier said examples of embodiments facing the back is closed off by probe wall 23.

Also in the example of an embodiment illustrated in FIG. 6, inner walls 25 are arranged inclined relative to one another, wherein the separation between the oppositely lying inner walls 25 in the cavity increases from front to back in the direction toward probe wall 23. The two electrodes 11d are also centrally arranged here on inclined inner walls 25 of inner space 3, and have concave inner surfaces, in each case, inclined in the direction of probe wall 23.

Instead of the concave electrodes 11c, 11d provided in the examples of embodiments illustrated in FIGS. 5 and 6, other suitable electrode shapes, in the sense of the invention, especially planar electrodes, can also naturally be applied.

Figure 7:
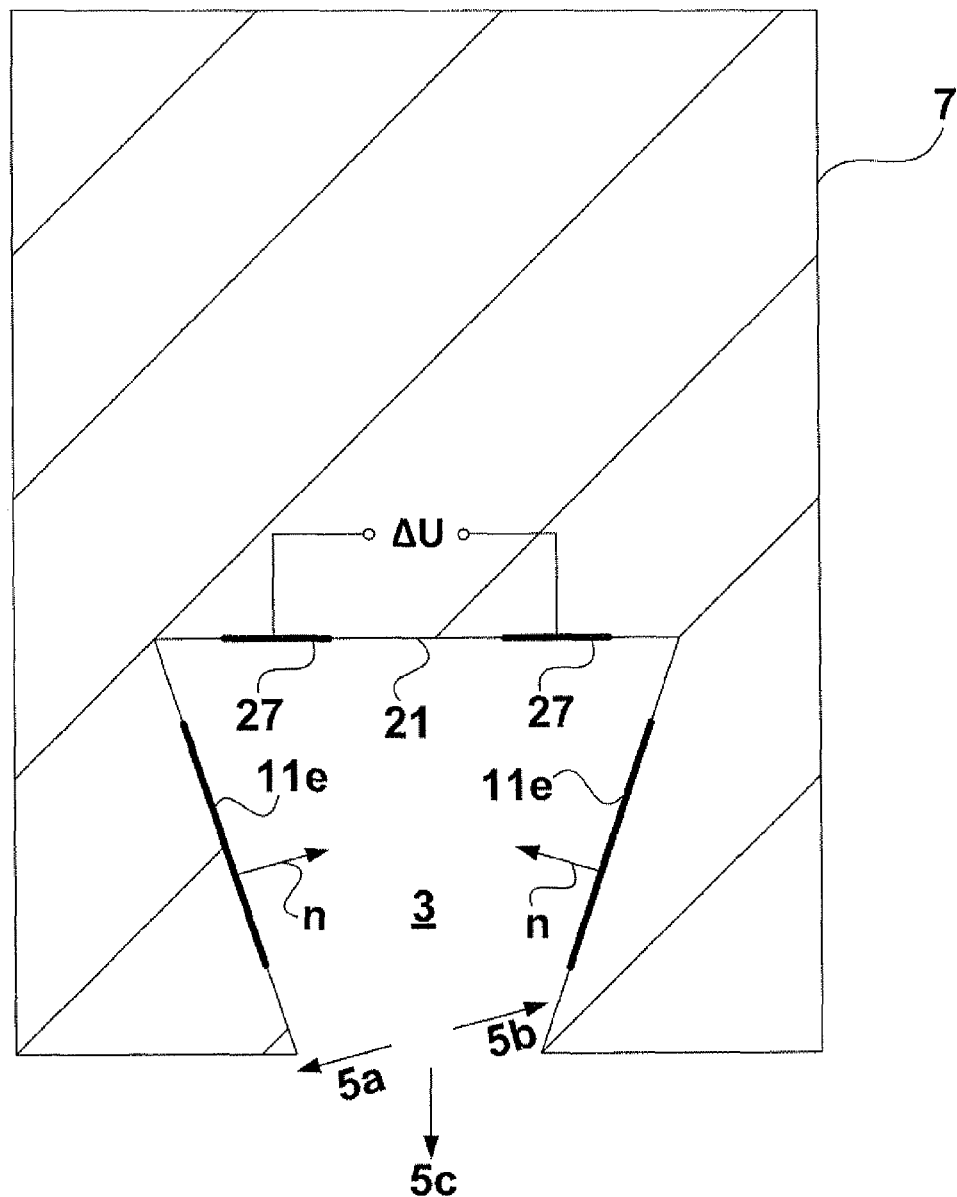
FIG. 7 is a conductivity probe having planar mutually opposing electrodes inclined relative to one another in the direction of an upper probe wall.

FIG. 7 shows, for this, a variation of the example of an embodiment illustrated in FIG. 5, which differs from the latter only in that instead of the concave electrodes 11c, the mutually opposing electrodes 11e provided here have planar inner surfaces inclined relative to one another and, in each case, are inclined in the direction of probe wall 21.

Figure 8:
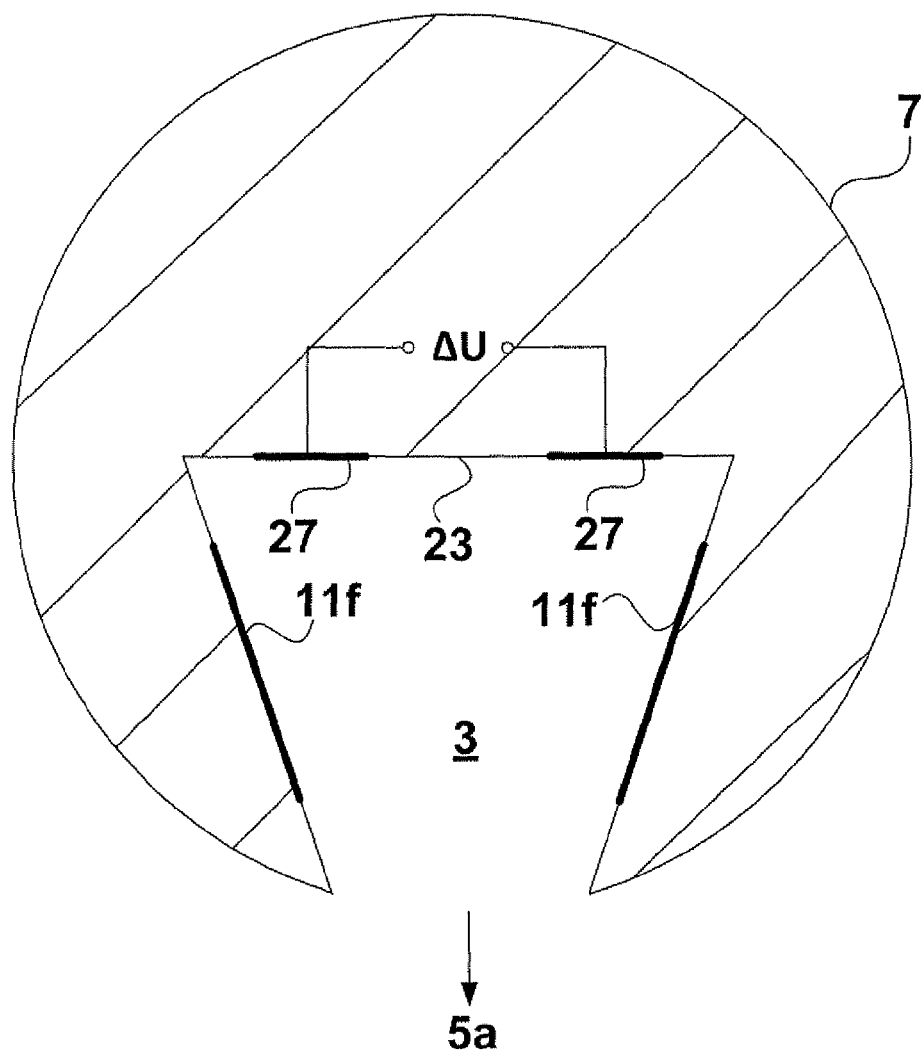
FIG. 8 is a conductivity probe having planar mutually opposing electrodes inclined relative to one another in the direction of a rear probe wall.

FIG. 8 shows, for this, a variation of the example of an embodiment illustrated in FIG. 6, which differs from the latter only in that instead of the concave electrodes 11d, the mutually opposing electrodes 11f provided here have planar inner surfaces inclined relative to one another and, in each case, inclined in the direction of probe wall 23.

Due to the inclination of electrodes 11e of the form of embodiment illustrated in FIG. 7, surface normals n on the planar inner surfaces point into inner space 3 in a direction away from lower opening 5c. Although here only the surface normals on the edge surfaces of electrodes 11e neighboring lower opening 5c point into inner space 3 in a direction away from this opening 5c, a clearly lower dependence of the conductivity probe on the separation from a neighboring object, such as e.g. a wall, is nevertheless shown here also.

FIG. 9 shows, in this connection, the dependencies of the normalized cell constants Z of conductivity sensor A having planar electrodes 11e inclined relative to one another in the direction of probe wall 21 illustrated in FIG. 7, in comparison to an otherwise equally constructed conductivity sensor B having planar electrodes arranged planparallel to one another, at a separation d from a conductive wall located below the respective sensors.

For comparison in the diagram, schematic diagrams of both conductivity sensors A and B are supplementally presented, in which the field lines, in each case, forming between the electrode pairs are drawn. From this, it is evident that a relatively low inclination of electrodes 11e into inner space in a direction facing away from opening 5c leads to the field lines remaining limited to a very narrow expansion region, while with a parallel orientation of electrodes, they clearly extend further out from inner space 3.

This is correspondingly reflected in a comparison of the normalized cell constants Z of both conductivity sensors A and B. Cell constant Z of conductivity sensor A of the invention increases clearly more slowly than that of conductivity sensor B as the distances d decreases. While both have the same normalized cell constant of Z=1 in the case of a separation d of 2 cm and greater, the cell constant Z of conductivity sensor A of the invention in the case of a separation of d=7 mm is only 1.2 while that of conductivity sensor B has already risen to a value of almost 1.4.

This comparatively high insensitivity of conductivity sensor A of the invention can be still further improved by applying, for example, the above described concave electrodes, or by providing on the sides of electrode 11e facing front opening 5a and rear opening 5b, in each case, an edge surface 17 on the adjoining planar base, wherein the edge surfaces 17 are inclined in a direction into inner space 3 and facing away from the respective adjoining openings 5a, 5b.

The invention can also be completely analogously applied to conductive four electrode, conductivity sensors, which— exactly as described in the case of the two electrode conductivity probes—have a probe 1, which is immersible in a measured medium and which contains an inner space 3 connected to an environment of the probe via at least one opening 5 and two electrodes 11 serving as electrical current electrodes, which electrodes 11 have inner surfaces directed toward inner space 3 and outwardly facing, outer surfaces covered by insulation. In measurement operation, an alternating electrical current can also be fed here to a medium located in inner space 3 via electrodes 11 by applying an alternating voltage to electrodes 11. The basic construction of probes 1 of four electrode conductivity sensors and the electrical current electrodes corresponds, thus, to that of the two electrode conductivity probes described above; consequently, such is not explained in detail again here.

In addition to the electrical current electrodes, four electrode conductivity sensors have two other electrodes, subsequently referred to as voltage electrodes 27, via which a potential difference ΔU due to the alternating current fed into the medium is tapped during measurement operation. Since the basic construction of four electrode conductivity sensors is compatible with that of the two electrode conductivity sensors described, no isolated examples of embodiments are presented in the figures. Instead, two additional voltage electrodes 27, which are naturally omitted in the corresponding two electrode conductivity sensors, are shown in FIGS. 5 to 8.

In accordance with the four electrode measuring principle, a measuring electronics 13 connected to electrodes 11 and to voltage electrodes 27 is provided here. This determines the impedance of the conductivity measurement cell from the fed in alternating electrical current and the potential difference ΔU preferably currentlessly measured by measuring electronics 13, and ascertains a specific resistance or a specific conductance of the medium located in the measuring cell from the potential difference ΔU based on a cell constant Z determined earlier, as resulting from the geometry and the character of the given measuring cell.

According to the invention, the inner surfaces of the two electrodes 11 supplied with alternating voltage during measurement operation again have edge surfaces neighboring at least one of the openings 5a, 5b, 5c. These edge surfaces also have a surface geometry directing the electric field lines beginning or ending thereon in a direction facing away from such opening 5a, 5b, or 5c and into the inner space. Preferably, all edge surfaces neighboring one of openings 5a, 5b, 5c are also embodied here in this manner of the invention. In this regard, the above explanations for electrodes 11 of the two electrode conductivity sensors correspondingly hold.

For four electrode conductivity sensors of the invention, the variants described above and illustrated in FIGS. 5 to 8 are preferably applied. In these variants, mutually opposing electrodes 11c, 11d, 11e, 11f supplied with alternating voltage are arranged inclined relative to one another so that the surface normals on the inner surfaces of electrodes 11c, 11d, 11e, 11f point in the direction of electrically insulating probe wall 21 or 23, which closes off the inner space 3 from the outside on one side.

In these variants, both voltage electrodes 27 are preferably arranged, as supplementally presented in FIGS. 5 to 8, in the interior of the measuring cell on probe wall 21 or 23, which terminates inner space 3. Therewith, on the one hand, there is a great measurement insensitivity to objects located in the vicinity of probe 1, this being due to the surface geometry of the electrodes 11c, 11d, 11e, 11f of the invention supplied with alternating electrical current, wherein the surface geometry directs field lines into the measurement cell interior, and, on the other hand, there is a large measurement effect, due to the directing of the field lines to probe wall 21, 23 effected by the inclination of electrodes 11c, 11d, 11e, 11f and therewith onto the voltage electrodes 27 arranged next to one another there.

The invention claimed is:

1. A conductive conductivity sensor, comprising:
a probe immersible in a measured medium, said probe has an inner space, which is connected to an environment of said probe via at least one opening leading out from said inner space, and in which are arranged two electrodes, which are supplied with an alternating voltage during measurement operation and which have inner surfaces facing into said inner space and outwardly facing outer surfaces covered by insulation, wherein:
said inner surfaces have edge surfaces adjoining said openings; and
at least the edge surfaces adjoining one of said openings have a surface geometry directing thereon beginning or ending, electric field lines in a direction facing away from said opening and into said inner space; and said surface geometry effects a targeted orientation and focusing of the field lines during measurement operation between said electrodes into said inner space of said probe.

2. The conductive conductivity sensor as claimed in claim 1, wherein:
all edge surfaces of said inner surfaces of the electrodes neighboring said openings have a surface geometry directing electric field lines, which begin or end thereon, in a direction facing away from said respective opening and into said inner space.

3. The conductive conductivity sensor as claimed in claim 1, wherein:
surface normals on the edge surfaces having said surface geometry point in a direction away from said respective opening and into said inner space.

4. The conductive conductivity sensor as claimed in claim 1, wherein:
said inner surfaces of said electrodes have a surface geometry, which focuses electric field lines into said inner space.

5. The conductive conductivity sensor as claimed in claim 4, wherein:
said inner surfaces of said electrodes are concave.

6. The conductive conductivity sensor as claimed in claim 1, wherein:
said electrodes have a planar base, on which adjoins, on at least one side neighboring one of said openings, an edge surface inclined in a direction facing away from said openings, and into said inner space.

7. The conductive conductivity sensor as claimed in claim 1, wherein:
said electrodes are arranged mutually opposing and inclined relative to one another; and
each of said electrodes has totally one orientation facing in a direction away from one and the same opening and into said inner space.

8. The conductive conductivity sensor as claimed in claim 7, further comprising:
an electrically insulating probe wall, wherein:
each of said electrodes is inclined in the direction of said electrically insulating probe wall, which closes off said inner space from the outside on one side.

9. The conductive conductivity sensor as claimed in claim 7, wherein:
said electrodes are electrical current electrodes, via which an alternating electrical current can be fed into a medium located in said inner space through application of an alternating voltage to said electrodes during measurement operation; and
in said inner space, two voltage electrodes are provided, via which an applied potential difference lying thereacross due to the alternating current applied to the medium can be tapped during measurement operation.

10. The conductive conductivity sensor as claimed in claim 8, wherein:
said voltage electrodes are arranged on said electrically insulating probe wall.

* * * * *